United States Patent [19]

Eggler et al.

[11] Patent Number: 4,738,972

[45] Date of Patent: Apr. 19, 1988

[54] HYPOGLYCEMIC THIAZOLIDINEDIONES

[75] Inventors: James F. Eggler, Stonington; Gerald F. Holland, Old Lyme; Michael R. Johnson, Gales Ferry; Robert A. Volkmann, Ledyard, all of Conn.

[73] Assignee: Pfizer Inc., New York, N.Y.

[21] Appl. No.: 67,899

[22] Filed: Jun. 26, 1987

Related U.S. Application Data

[63] Continuation-in-part of Ser. No. 10,081, Dec. 29, 1986, Pat. No. 4,703,052.

[51] Int. Cl.⁴ .................. C07D 417/10; C07D 277/34; A61K 31/425; A61K 31/47
[52] U.S. Cl. .................................... 514/314; 514/369; 546/165; 546/166; 546/167; 546/280; 548/183
[58] Field of Search ................ 548/183; 546/165, 166, 546/167, 280; 514/314, 364

[56] References Cited

U.S. PATENT DOCUMENTS

| | | | |
|---|---|---|---|
| 4,340,605 | 7/1982 | Kawamatsu et al. | 424/263 |
| 4,376,777 | 3/1983 | Kawamatsu et al. | 424/270 |
| 4,461,902 | 7/1984 | Kawamatsu et al. | 548/183 |
| 4,572,912 | 2/1986 | Yoshioka | 514/369 |

FOREIGN PATENT DOCUMENTS

| | | | |
|---|---|---|---|
| 8423287 | 7/1984 | Australia | 514/314 |
| 8203 | 2/1980 | European Pat. Off. | 514/314 |
| 84926 | 8/1983 | European Pat. Off. | 514/314 |
| 139421 | 5/1985 | European Pat. Off. | 514/314 |

*Primary Examiner*—Robert Gerstl
*Attorney, Agent, or Firm*—Peter C. Richardson; Albert E. Frost; Robert K. Blackwood

[57] ABSTRACT

Hypoglycemic 5-[1-(5,6,7,8-tetrahydro-2-napthyl-; 1,2,3,4-tetrahydro-6-quinolyl-; 2-indanyl-; and 2-indolyl)alkyl]thiazolidine-2,4-dione derivatives, pharmaceutically acceptable salts thereof, and a method for their use in the treatment of hyperglycemic mammals.

23 Claims, No Drawings

HYPOGLYCEMIC THIAZOLIDINEDIONES

This application is a continuation-in-part of co-pending application Ser. No. 07/010,081, filed Dec. 29, 1986, now U.S. Pat. No. 4,703,052, claiming priority to PCT application no. PCT/US85/00962, filed May 21, 1985.

BACKGROUND OF THE INVENTION

The present invention relates to certain compounds of the formula (I), depicted below, having utility as hypoglycemic agents, methods for their use and pharmaceutical compositions containing them.

In spite of the early discovery of insulin and its subsequent wide-spread use in the treatment of diabetes, and the later discovery and use of sulfonylureas (e.g. chlorpropamide, tolbutamide, acetohexamide, tolazamide) and biguanides (e.g. phenformin) as oral hypoglycemic agents, the treatment of diabetes remains less than satisfactory. The use of insulin, necessary in about 10% of diabetic patients in which synthetic hypoglycemic agents are not effective (Type I diabetes, insulin dependent diabetes mellitus), requires multiple daily, usually self injection. Determination of the proper dosage of insulin requires frequent estimations of the sugar in the urine or in the blood. The administration of an excess dose of insulin causes hypoglycemia, with effects ranging from mild abnormalities in blood glucose or coma, or even death. Treatment of non-insulin dependent diabetes mellitus (Type II diabetes) usually consists of a combination of diet, exercise, oral agents, e.g., sulfonylureas, and in more severe cases, insulin. However, the clinically available hypoglycemics are unfortunately fraught with other toxic manifestations which limit their use. In any event, where one of these agents may fail in an individual case, another may succeed. A continuing need for hypoglycemic agents, which may be less toxic or succeed where others fail, is clearly evident.

In addition to the hypoglycemic agents cited above, a variety of other compounds have been reported to possess this type of activity, as reviewed recently by Blank [Burger's Medicinal Chemistry, Fourth Edition, Part II, John Wiley and Sons, N.Y. (1979), pp. 1057-1080].

U.S. Pat. No. 4,342,771 discloses a class of oxazolidinedione hypoglycemic agents of the general formula

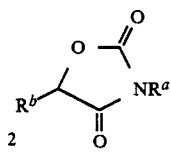

where $R^a$ is H or certain acyl groups and $R^b$ is certain mono- or bicyclic heterocyclic groups.

European Patent Application No. 117,035 discloses a group of 5-phenylthiazolidine-2,4-dione hypoglycemic agents of the formula

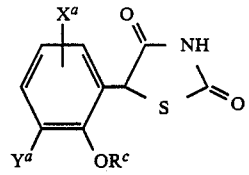

where $R^c$ is lower alkyl, $X^a$ is F, Cl or Br and $Y^a$ is H, Cl, lower alkyl or lower alkoxy. U.S. Pat. No. 4,461,902 discloses certain 5-[(4-cyclohexylmethoxyphenyl) methyl]thiazolidine-2,4-dione hypoglycemic agents of the formula

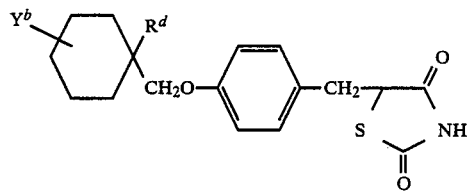

where $R^d$ is H or lower alkyl and $Y^b$ is an oxo or hydroxy group.

SUMMARY OF THE INVENTION

The present invention relates of compounds of the formula

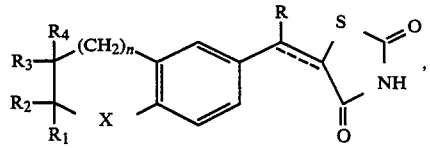

a pharmaceutically acceptable cationic salt thereof, or a pharmaceutically acceptable acid addition salt thereof when the compound contains a basic nitrogen, wherein the broken line is a bond or no bond, n is zero, 1, or 2; X is $CH_2$, $C=O$, CHOH or $NR_5$, where $R_5$ is hydrogen, $(C_1-C_6)$ alkyl optionally substituted by OH, Cl, Br, $OR_6$ or $COOR_6$, $(CH_2)_xC_6H_5$ optionally substituted on $C_6H_5$ by OH, Cl, Br, $OR_6$ or $COOR_6$, formyl, $(C_2-C_5)$akanoyl, $CO(CH_2)_xC_6H_5$, or $COOR_6$; where x is zero or an integer from 1 to 3 and $R_6$ is benzyl or $(C_1-C_4)$alkyl;

R is H, $CH_3$ or $C_2H_5$;

when taken separately, $R_1$ is H, $(C_5-C_7)$cycloalkyl, $(C_6-C_8)$methylsubstituted cycloalkyl, pyridyl, thienyl, furyl, naphthyl, p-biphenylyl, tetrahydrofuranyl, tetrahydrothienyl, tetrahydropyranyl, $C_6H_4W_2$ or alk-$W_1$ and alk is $(C_1-C_6)$ alkylene, ethylidene or isopropylidiene; $W_1$ is H, OH, $(C_1-C_4)$alkoxy, $(C_1-C_4)$thioalkyl, pyridyl, furyl, thienyl, tetrahydrofuryl, tetrahydrothienyl, naphthyl, $(C_5-C_7)$cycloalkyl or $C_6H_4W_2$ and $W_2$ is H, OH, F, Cl, Br, $(C_1-C_4)$alkyl, $(C_1-C_4)$alkoxy or $(C_1-C_4)$thioalkyl; $R_2$ is H or $CH_3$, $R_3$ is H, $(C_1-C_6)$ alkyl, $C_6H_4W_2$ or benzyl; and $R_4$ is H;

when $R_1$ and $R_2$ are taken together they form $(C_4-C_6)$alkylene and $R_3$ and $R_4$ are each H;

when $R_3$ and $R_4$ are taken together they form $(C_4-C_6)$ and $R_1$ and $R_2$ are each H; and when $R_2$ and $R_3$ are taken together they are $(C_3-C_4)$alkylene and $R_1$ and $R_4$ are each H.

Preferred compounds are those wherein the broken line is no bond and R is H. Preferred values for $R_1$, $R_2$, R₃ and R₄ are either R₂, R₃ and R₄ are each hydrogen and R₁ is hydrogen, phenyl or benzyl, or R₁ and R₂ are each hydrogen and R₃ and R₄ are taken together as (CH₂)₄. The preferred value of n is 1. When X is NR₅, the preferred values of R₅ are methyl, benzyl, 2-phenylethyl, and 2-(4-benzyloxyphenyl)ethyl.

The compounds of the invention are useful as hypoglycemic agents and are mechanistically distinct from known hypoglycemics (the sulfonylureas) currently employed in diabetic therapy. Preferred invention compounds because of their ease of preparation and excellent hypoglycemic activity in mammals are:

5-[1-(2-(4-benzyloxyphenyl)ethyl)-1,2,3,4-tetrahydro-6-quinolyl]methyl]thiazolidine-2,4-dione;

5-[6-benzyl-5,5,7,7-tetrahydro-2-naphthyl)-methyl]-thiazolidine-2,4-dione;

5-[(1-benzyl-1,2,3,4-tetrohydro-6-quinolyl)-methyl]-thiazolidine-2,4-dione;

5-[(1-(2-phenylethyl)-1,2,3,4-tetrahydro-6-quinolyl)methyl]thiazolidine-2,4-dione;

5-[(1,2-dibenzyl-1,2,3,4-tetrahydro-6-quinolyl)methyl]-thiazolidine-2,4-dione;

5-[(2-benzyl-1-methyl-1,2,3,4-tetrahydro-6-quinolyl)-methyl]thiazolidine-2,4-dione;

5-[(1-methyl-1,2,3,4-tetrahydro-6-quinolyl) methyl]-thiazolidine-2,4-dione;

5-[(2-benzyl-l(2-phenylethyl)-1,2,3,4-tetrahydro-6-quinolyl)methyl]thiazolidine-2,4-dione;

5-[(1-methyl-2-phenyl)-1,2,3,4-tetrahydro-6-quinolyl)-methyl]thiazolidine-2,4-dione;

5-[([1-benzyl-1,2,3,4-tetrahydroquinoline-3-spirocyclopentane]-6-yl)methyl]thiazolidine-2,4-dione;

5-[(2-benzyl-1,2-dihydronaphthalen-1(2H)-on-6-yl)methyl]thiazolidine-2,4-dione; and 5-[6-benzyl-5-hydroxy-5,6,7,8-tetrahydro-2-naphthyl]-thiazolidine-2,4-dione.

The expression "pharmaceutically acceptable cationic salts" is intended to define such salts as the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine) diethylamine, piperazine, tromethamine (2-amino-2-hydroxymethyl1,3-propanediol), procaine, etc. An especially preferred such salt is the sodium salt.

Mixtures of optically active isomers, and partially or completely optically resolved isomers of the compounds claimed herein are within the scope of the present invention.

Also embraced by the present invention are pharmaceutical compositions for use in treating a hyperglycemic mammal which comprises a blood glucose lowering amount of a compound of formula (I) and a pharmaceutically acceptable carrier. The invention further comprises a method of lowering blood glucose in a hyperglycemic mammal which comprises administering to a mammal in need of such treatment a blood glucose lowering effective amount of a compound of formula (I).

The compounds of formula (I) contain asymmetric centers at the 2-position, when R₁ and R₂ are different, and at the 3-position, when R₃ and R₄ are different. The compounds of formula (I) wherein the broken line is no bond have additional asymmetric centers at the R-bearing carbon atoms linking the two rings, when R is methyl or ethyl; and at the 5-carbon of the thiazolidine-dione group. Among the enantiomers of a given compound, one will ordinarily be favored over the others and over the racemates because of its greater activity. The present invention is considered to embrace the racemates, diastereomeric mixtures, and the pure enantiomers and diastereomers of the compounds of formula (I), the utility of which is determined by the biological evaluations described below.

DETAILED DESCRIPTION OF THE INVENTION

The compounds of the invention are prepared, for example, by the method of Synthetic Scheme A, below

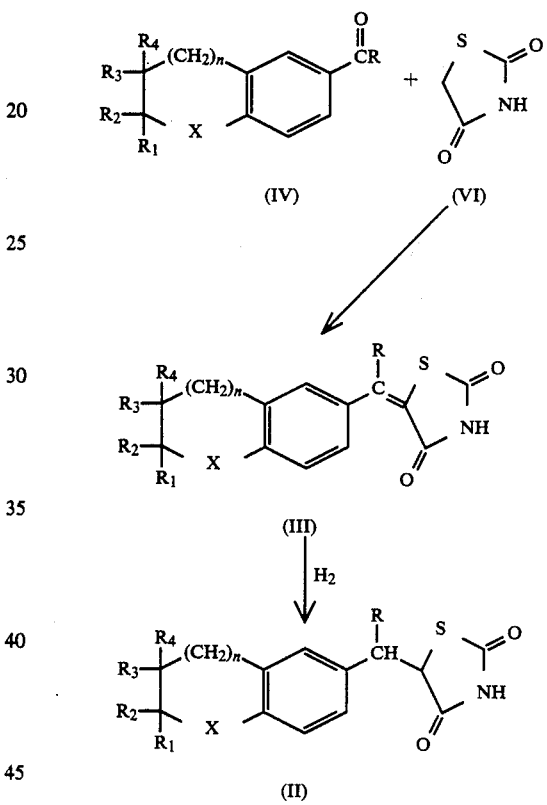

In the first step, approximately equimolar amounts of the reactant (IV), wherein n, R, R₁–R₄ and X are as defined above, and thiazolidinedione (VI) are heated in the presence of a mild base to provide the olefin of formula (III). When X is C=O, the carbonyl group is preferably in protected form, e.g., as a ketal, preferably as the cyclic ketal formed with ethylene glycol. While this step may be carried out in the presence for a reaction inert solvent, it is preferably carried out in the absence of solvent at a temperature which is sufficiently high to cause at least partial melting of the reaction mixture. A preferred such temperature is in the range of from 100 to 250° C., and especially preferred is a temperature of from 140 to 200° C.

Examples of suitable mild bases for the above reaction include the alkali metal and alkaline earth salts of weak acids such as the (C₁–C₁₂)alkyl carboxylic acids and benzoic acid; alkali metal and alkaline earth carbonates and bicarbonates such as calcium carbonate, magnesium carbonate, potassium bicarbonate; and tertiary amines such as pyridine, N-methymorpholine, N-ethylpiperidine and the like. An especially preferred mild base is sodium acetate for reasons of economy and efficiency.

In a typical such reaction the aldehyde or ketone starting material (IV) and thiazolidinedione (VI) are combined in approximately equimolar amounts with a molar excess, preferably a 2–4 fold molar excess, of anhydrous sodium acetate and the mixture is heated at a temperature high enough to effect melting, at which temperature the reaction is substantially complete in from about 5 to 60 minutes. The desired olefin of formula (III) is then isolated, for example, by mixing with water and filtration, to obtain the crude product, which is purified, if desired, e.g. by crystallization or by standard chromatographic methods.

The olefinic products of formula (III) are active hypoglycemic agents and also serve as intermediates for preparation of the corresponding reduced compounds of formula (II). While the reduction of the above olefins may be carried out by employing a wide variety of reducing agents which are known to reduce carbon-to-carbon double bonds, the preferred methods employ hydrogen in the presence of a noble metal catalyst, or conventional reduction with sodium amalgam, or magnesium metal in methanol.

When the reduction step is carried out employing hydrogen in the presence of a noble metal catalyst, a convenient method for carrying out this transformation is to stir or shake a solution of a compound of the formula (III) in a reaction inert solvent under an atmosphere of hydrogen, or hydrogen mixed with an inert diluent such as nitrogen, in the presence of a noble metal hydrogenation catalyst. Suitable solvents for this reaction are those which substantially dissolve the starting compound of the formula (III) but which do not themselves suffer hydrogenation or hydrogenolysis. Examples of such solvents include ethers such as diethyl ether, tetrahydrofuran, dioxane and 1,2-dimethoxyethane; low molecular weight amides such as N,N-dimethylformamide, N,N-dimethylacetamide and N-methylpyrrolidone; and lower alkyl carboxylic acids such as formic, acetic, propionic and isobutyric acid. An especially preferred such solvent is glacial acetic acid.

Introduction of the hydrogen gas into the reaction medium is usually accomplished by carrying out the reaction in a sealed vessel, containing the compound of formula (III), the solvent, the catalyst and the hydrogen. The pressure inside the reaction vessel can vary from about 1 to about 100 kg/cm$^2$. The preferred pressure range, when the atmosphere inside the reaction vessel is substantially pure hydrogen, is from about 2 to about 5 kg/cm$^2$. The hydrogenation is generally run at a temperature of from about 0° to about 60° C., and preferably from about 25° to about 50° C. Utilizing the preferred temperature and pressure values, hydrogenation generally takes place in a few hours, e.g. from about 2 hours to about 20 hours. The preferred noble metal catalysts used in this hydrogenation reaction are the type of agents known in the art for this kind of transformation, for example, nickel, palladium, platinum and rhodium. A palladium catalyst is preferred because such catalysts are not readily poisoned by sulfur. The catalyst is usually present in an amount from about 0.01 to about 25 weight-percent, and preferably from about 0.1 to about 10 weight-percent, based on the compound of formula (III). It is often convenient to suspend the catalyst on an inert support; a particularly convenient catalyst is palladium suspended on an inert support such as carbon.

When the hydrogenation of the methylene double bond is substantially complete, the desired product of formula (II) is then isolated by standard methods, e.g. the catalyst is removed by filtration, the solvent evaporated and the product purified, if desired, by well known methods such as crystallization or by chromatography. When in the compound of the formula (II) X is carbonyl (or the protected ketal form thereof) or carbinol (CHOH), more complete hydrogenation will produce the compound of the formula (II) wherein X is methylene (CH$_2$) Similarly, when X is NR$_5$ and R$_5$ is carbonbenzoxy or benzyl in the compound (III), more complete hydrogenation will produce the compound (II) wherein X is NH.

Ketal protecting groups are readily removed by conventional acid catalyzed hydrolysis, as exemplified below, to form those compounds of the formula (II) or (III) wherein X is C=O.

Since hydrogenation methods have a well-known tendency to cleave benzylic carbon-oxygen and carbon-nitrogen bonds, the more preferred method for reduction of the compounds of the formula (III), wherein X is CHOH, C=O (or ketal), or NR$^5$ when R$^5$ is carbobenzoxy or benzyl, is conventional sodium amalgam or metallic magnesium reduction in methanol, usually at or about ambient temperature, as exemplified below.

Furthermore, those compounds wherein X is CHOH (carbinol) are preferably prepared by conventional sodium borohydride reduction of the corresponding compound wherein X is C=O; and those compounds wherein X is NR$_5$ and R$_5$ is (C$_2$–C$_5$)alkanoyl, CO(CH$_2$)$_x$C$_6$H$_5$, COOR$_6$ or benzyloxycarbonyl are preferably prepared by conventional acylation of a corresponding compound wherein X is —NH.

The pharmaceutically acceptable cationic salts of the compounds of the present invention are readily prepared by reacting the acid forms with a appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In some cases, salts can be prepared by mixing a solution of the acid with a solution of a different salt of the cation (sodium ethylhexanoate, magnesium oleate), employing a solvent in which the desired cationic salt precipitates, or can be otherwise isolated by concentration and/or addition of a non-solvent.

2,4-thiazolidinedione (VI) is commercially available. The aldehydes and ketones of formula (IV) are prepared by a variety of well known methods, for example, by mild oxidation of the corresponding primary or secondary alcohol with reagents such as manganese dioxide or chromic acid under compositions known to produce aldehydes from primary alcohols and ketones from secondary alcohols; reaction of the corresponding bromine substituted bicyclic hydrocarbon with n-butyl lithium followed by N,N-dimethylformamide at −80° to −70° C.; and other methods well known in the art.

The requisite bromo-substituted and hydroxyalkyl-substituted compounds, described above as precursors of the starting aldehydes and ketones of formula (IV), are prepared by a variety of methods known in the art and illustrated in the Preparations, below.

The reactions employed to prepare the compounds of this invention can generally be monitored by standard tlc methods, employing commercially available plates. Suitable eluants are common solvents such as chloroform, ethyl acetate or hexane or suitable combinations thereof which will differentiate starting materials, product, by-products, and in some cases intermediates. Applying these methods, which are well known in the art, will permit further improvement in the methodology of the specific examples detailed hereinafter, e.g. the selection of more optimal reaction times and temperatures, as well as aid in the selection of optimal processes.

The thiazolidine-2,4-diones of the present invention are readily adapted to clinical use as antidiabetic agents. The activity required for this clinical use is defined by the test for hypoglycemic effect in ob/ob mice by the following procedure:

Five to eight week old C57 BL/6J-ob/ob mice (obtained from Jackson Laboratory, Bar Harbor, Maine) were housed five per cage under standard animal care practices. After a one week acclimation period, the animals were weighted and 25 microliters of blood was collected via an ocular bleed prior to any treatment. The blood sample was immediately diluted 1:5 with saline containing 2.5 mg/ml sodium fluoride and 2% sodium heparin, and held on ice for metabolite analysis. Animals were then dosed daily for five days with drug (5–50 mg/kg), a positive control (50 mg/kg) of ciglitazone; U.S. Pat. No. 4.467,,902; Sohda et al., Chem. Pharm. Bull., vol. 32, pp. 4460–4465, 1984), or vehicle All drugs were administered in a vehicle consisting of 0.25% w/v methyl cellulose. On day 5, the animals were weighed again and bled (via the ocular route) for blood metabolite levels. The freshly collected samples were centrifuged for two minutes at 10,000 ×g at room temperature. The supernatant was analyzed for glucose, for example, by the ABA 200 Bichromatic Analyzer*, using the A-gent* glucose UV reagent system** (hexokinase method) using 20, 60 and 100 mg/dl standards. Plasma glucose was then calculated by the equation, Plasma glucose (mg/dl)=Sample value×5×1.67=

8.35×Sample value where 5 is the dilution factor and 1.67 is the plasma hematocrit adjustment (assuming the hematocrit is 40%).

*A registered trademark of Abbott Laboratories, Diagnostics Division, 820 Mission Street, So. Pasadena, CA 91030.
**A modification of the method of Richterich and Dauwalder, Schweizerische Medizinische Wochenschrift, 101, 860 (1971).

The animals dosed with vehicle maintain substantially unchanged hyperglycemic glucose levels (e.g., 250 mg/dl), while positive control animals have depressed glucose levels (e.g., 130 mg/dl). Test compounds are reported in terms of % glucose normalization. For example, a glucose level which is the same as the positive control is reported as 100%.

The thiazolidine-2,4-diones of the present invention are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg/kg body weight of the subject per day, preferably about 0.10 to about 10 mg/kg body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

The compounds can be used in pharmaceutical preparations containing the compound, or pharmaceutically acceptable acid salt thereof, in combination with a pharmaceutically acceptable carrier or diluent. Suitable pharmaceutically acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically acceptable acid addition salts of the compounds. The injectable solutions prepared in this manner can then be administered intravenously, intraperitoneally, subcutaneously, or intramuscularly, with intramuscular administration being preferred in man.

The present invention is illustrated by the following Examples. However, it should be understood that the invention is not limited to the specific details of these examples. Nomenclature used herein is based on Rigaudy and Klesney, IUPAC Nomenclature of Organic Chemistry, 1979 Ed., Pergammon Press, New York, 1979.

EXAMPLE 1

6-Benzyl-5,6,7,8-tetrahydro-2-naphthalene-carbaldehyde

2-Benzyl-6-bromo-1,2,3,4-tetrahydronaphthalene (1.5 g, 0.005 mol) was dissolved in 30 ml tetrahydro-furan and cooled to −78° C. under dry $N_2$. Butyl lithium (2.32 ml of 2.14 M in hexane, 0.005 mol) was added and the mixture stirred at −70° C. for 1 hour. Dimethyl-formamide (0.39 ml, 0.005 mol) was then added dropwise and the mixture stirred at −70° C. for 2 hours, allowed to warmed toward room temperature for 0.5 hour, poured slowly into 38 ml of ice cold 1N HCl and extracted 2×50 ml ethyl acetate. The combined organic layers were washed with brine, dried (MgSO$_4$) and stripped in vacuo to yield title product as an oil, 1.26 g; tlc Rf 0.6 (4:1 hexane:ethyl acetate).

EXAMPLE 2

5-[(6-Benzyl-5,6,7,8-tetrahydro-2-naphthyl) methylene]thiazolidine-2,4-dione

The title product of the preceding Example (1.26 g, 0.005 mol), sodium acetate (1.02 g, 0.0125 mol) and thiazolidine-2,4-dione (0.73 g, 0.0062 mol) were combined, intimately mixed and held in a preheated oil bath at 140° C. for 20 minutes, during which time the mixture solidified. The solid was cooled to room temperature, pulverized, stirred in 15 ml of H₂O for 15 minutes, filtered and the solids dried in high vacuo at 60° C. for 45 minutes to yield present title product, 1.4 g; tlc Rf 0.7 (1:1 ethyl acetate:hexane).

EXAMPLE 3

5-(6-Benzyl-5,6,7,8-tetrahydro-2-naphthylmethyl)-thiazolidine-2,4-dione

The title product of the preceding Example (1.2 g, 0.0034 mol) was dissolved by warming in 150 ml of glacial acetic acid. 10% Pd/C (1.2 g) was added and the mixture hydrogenated at four atmospheres for two days. The mixture was warmed, catalyst recovered by filtration over diatomaceous earth, and the filtrate stripped to an oil. The oil was restripped from 100 ml toluene and then 100 ml of ether, and finally flash chromatographed on a short column of silica gel using ether as eluant and discarding less polar impurities. Pure product fractions were combined and stripped to yield title product as a gummy white solid, 0.9 g; tlc Rf 0.3 (2:1 hexane:ether).

Example 4

5-(6-Benzyl-5,6,7,8-tetrahydro-2-naphthylmethyl)-thiazolidine-2,4-dione, Sodium Salt The product of the preceding Example (0.9 g, 0.0026 mol) was dissolved in 40 ml of methanol. Sodium methoxide (0.138 g, 0.0026 mol) was added and the mixture stirred at room temperature for 5 hours. The solvent was evaporated under a stream of N₂. The residual white solids were reslurried in 25 ml of ether and refiltered to yield title product, 0.84 g (87%), m.p. greater than 285° C; mass spectrum includes peaks at 351, 291, 276, 235, 200, 143, 128 and 92.

EXAMPLE 5

1-Benzyl-1,2,3,4-tetrahydro-6-quinolinecarbaldehyde

To dimethylformamide (1.7 ml, 0.022 mol) at 0° C. was added dropwise POCl₃ (2.0 ml, 0.022 mol) and the mixture allowed to warm and stirred at ambient temperature for 20 minutes, then diluted with 1,2-dichloroethane (5 ml). 1-Benzyl-1,2,3,4-tetrahydroquinoline (4.5 g, 0.020 mol) dissolved in 5 ml of 1,2-dichloroethane was then added and the mixture refluxed 1 hour, then cooled to room temperature. Sodium acetate (9.0g, 0.11 mol), dissolved in the minimum necessary water, was added and the mixture refluxed for 15 minutes. The layers were separated and the aqueous layer extracted 2×10 ml ether.

The combined organic layers were carefully washed (gas evolution) to pH 8 with saturated NaHCO₃, dried (K₂CO₃) and evaporated in vacuo to yield title product, 4.83 g. Twice recrystallized from ethyl acetate/cyclohexane showed mp 74°-75° C.

Anal. Calcd. for $C_{17}H_{17}NO$: C, 81.24; H, 6.82; N, 5.57. Found: C, 80.86, H, 6.76; N, 5.40.

EXAMPLE 6

5-[(1-Benzyl-1,2,3,4-tetrahydro-6-quinolyl)methylene]-thiazolidine-2,4-dione

The title product of the preceding Example (1.76 g, 0.0070 mol), thiazolidine-2,4-dione (1.02 g, 0.0088 mol) and sodium acetate (1.435 g, 0.0175 mol) were intimately mixed and heated in an oil bath at 140° C. for 0.5 hour. The resulting solid mass was cooled to room temperature and triturated 3×10 ml H₂O. The solids were dried under high vacuum, then triturated with 25 ml CH₃OH to yield present title product, 0.69 g; m.p. 230° C. (sinter), 242°-250° C. (dec).

Anal. Calcd. for $C_{20}H_{18}N_2O_2S$: C, 68.55; H, 5.18; N, 7.99. Found: C, 68.94; H, 5.02; N, 7.62.

Example 7

5-(1-Benzyl-1,2,3,4-tetrahydro-6-quinolylmethyl)-thiazolidine-2,4-dione

The title product of the preceding Example (0.60 g) was suspended in methanol (25 ml) under N₂. Ground 3% Na-Hg amalgam (12.7 g) was added and the mixture stirred for 3 hours. The suspension was decanted from a heavy grey precipitate and sufficient glacial acetic acid added to the decant to dissolve all remaining suspended material. The resulting solution was concentrated to dryness and the residue flash chromatographed on a 5 cm ×50 mm column of silica gel using 1:39 CH₃OH:CHCl₃ as eluant. The eluate was evaporated to a powder, 0.48 g, which was recrystallized from ethyl acetate and cyclohexane to yield purified title product, 0.31 g, mp 155°-157.5° C.

Anal. Calcd. for $C_{20}H_{20}N_2O_2S$: C, 68.15; H, 5.72; N, 7.95. Found: C, 68.39; H, 5.83; N, 7.72.

EXAMPLE 8

5-(1-Benzyl-1,2,3,4-tetrahydroquinolylmethyl)thiazolidine-2,4-dione, Sodium Salt To title product of the preceding Example (0.27 g, 0.0077 mol) in ethyl acetate (5 ml) was added sodium ethylhexanoate (0.14 g, 0.0084 mol). The mixture was stirred for 1 hour and title product recovered by filtration with ethyl acetate wash, 0.19 g; mp greater than 250° C.

Anal. Calcd. for $C_{20}H_{19}N_2O_2SNa$: C, 64.15; H, 5.12; N, 7.48. Found: C, 63.81; H, 4.91; N, 7.33.

EXAMPLE 9

1-(2-Phenylethyl)-1,2,3,4-tetrahydro-6-quinolinecarbaldehyde

By the method of Example 5, 1-(2-phenylethyl)-1,2,3,4-tetrahydroquinoline (4.99 g, 0.020 mol) was converted to present title product, as an oil, 5.6 g.

EXAMPLE 10

5-[1-(2-Phenylethyl)-1,2,3,4-tetrahydro-6-quinolyl)methylene]thiazolidine-2,4-dione Title product of the preceding Example (2.52 g, 0.0095 mol), thiazolidine-2,4-dione (1.45 g, 0.0124 mol) and sodium acetate (2.03 g, 0.0247 mol) were intimately mixed and heated in an oil bath at 140° C. for 40 minutes, then cooled to room temperature and the resulting solids triturated with 50 ml H₂O, stirred for 30 minutes, filtered, and air dried to yield 3.7 g of solids. The latter was triturated with 20 ml of hot CH₃OH and filtered to yield purified title product, 2.43 g; m. p. 211-213 (dec).

Anal. Calcd. for $C_{21}H_{20}N_2O_2S$: C, 69.20; H, 5.53; N, 7.69. Found: C, 68.95; H, 5.39; N, 7.42.

Example 11

5-[1-(2-Phenylethyl)-1,2,3,4-tetrahydro-6-quinolylmethyl]thiazolidine-2,4-dione

According to the method of Example 7, title product of the preceding Example (1.0 g) was converted to crude product. The latter was purified not by chromatography, but by refluxing with 75 ml ethyl acetate for 10 minutes, clarifying by filtration, and stripping the resulting filtrate to obtain title product as an oil, 0.75 g.

EXAMPLE 12

5-[1-(2-Phenylethyl)-1,2,3,4-tetrahydro-6-quinolylmethyl]thiazolidine-2,4-dione, Sodium Salt By the method of Example 8, title product of the preceding Example (0.55 g) was converted to present title product, 0.37 g; mp greater than 250° C.

Anal. Calcd. for $C_{21}H_{21}N_2O_2SNa$: C, 64.93; H, 5.45; N, 7.21. Found: C, 63.84; H, 5.22; N, 7.06.

EXAMPLE 13

1,2-Dibenzyl-1,2,3,4-tetrahydro-6-quinolinecarbaldehyde

By the method of Example 5, 1,2-dibenzyl-1,2,3,4-tetrahydroquinoline (0.89 g, 0.0028 mol) was converted to present title product as an oil, 0.93 g. The latter was further purified by radial chromatography on thick plates of silica gel, eluting with $CHCl_3$. The major band gave purified title product, 0.54 g, still as an oil; tlc Rf 0.25 ($CHCl_3$).

EXAMPLE 14

5-[(1,2-Dibenzyl-1,2,3,4-tetrahydro-6-quinolyl)methylene]thiazolidine-2,4-dione

The title product of the preceding Example (0.52 g, 0.0015 mol), thiazolidine-2,4-dione (0.23 g, 0.0020 mol) and sodium acetate (0.32 g, 0.0039 mol) were intimately mixed, heated in an oil bath at 140° C. for 2.5 hours, and cooled to room temperature. The resulting solids were suspended in 25 ml of $H_2O$, filtered and the solids dried under high vacuum, 0.52 g. Recrystallization from methanol gave purified title product, 0.27 g; m. p. 199°-201° C.

EXAMPLE 15

5-[(1,2-Dibenzyl-1,2,3,4-tetrahydro-6-quinolyl)methyl]thiazolidine-2,4-dione

Title product of the preceding Example (0.215 g) was reduced with sodium amalgam according to the method of Example 7. Following the stripping of the methanol, the residue was taken up in 25 ml $H_2O$, and the resulting solution acidified to pH 4 with 1N HCl and extracted 3×25 ml $CH_2Cl_2$. The organic layers were combined, dried ($MgSO_4$) and stripped to yield present title product as a dry foam, 180 mg; used directly in the next step.

EXAMPLE 16

5-[(1,2-Dibenzyl-1,2,3,4-tetrahydro-6-quinolyl)methyl]thiazolidine-2,4-dione, Sodium Salt By the method of Example 4, title product of the preceding Example (0.14 g) was converted to present title product, 68 mg; m.p. 110°-120° C. (decomp.).

EXAMPLE 17

2-Benzyl-1-methyl-1,2,3,4-tetrahydro-6-quinolinecarbaldehyde

By the method of Example 5, 2-benzyl-1-methyl-1,2,3,4-tetrahydroquinoline (1.5 g, 0.0063 mol) was converted to present title product as an oil, 1.66, purified by chromatography according to Example 13 to yield purified title product, 1.29 g.

EXAMPLE 18

5-[(2-Benzyl-1-methyl-1,2,3,4-tetrahydro-6-quinolyl)methylene]thiazolidine-2,4-dione By the method of Example 6, title product of the preceding Example (1.24 g, 0.0047 mol) was converted to present title product, 1.14 g; mp 214°-217° C.

Anal. Calcd. for $C_{21}H_{20}N_2O_2S$: C, 69.20; H, 5.53; N, 7.69. Found: C, 68.80; H, 5.18; N, 7.31.

EXAMPLE 19

5-[(2-Benzyl-1-methyl-1,2,3,4-tetrahydro-6-quinolyl)methyl]thiazolidine-2,4-dione By the method of Example 15, title product of the preceding Example (1.0 g) was converted to present title product as an oil, 1.03 g.

EXAMPLE 20

5-[(2-Benzyl-1-methyl-1,2,3,4-tetrahydro-6-quinolyl)methyl]thiazolidine-2,4-dione, Sodium Salt By the method of Example 8, title product of the preceding Example (0.81 g, 0.0022 mol) was converted to present title product, 0.60 g; mp greater than 280° C.

Anal. Calcd. for $C_{21}H_{21}N_2O_2SNa$: C, 64.93; H, 5.45; N, 7.21. Found: C, 64.48; H, 5.11; N, 7.19.

EXAMPLE 21

1-Methyl-1,2,3,4-tetrahydro-6-quinoline carbaldehyde

By the method of Example 5, 1-methyl-1,2,3,4-tetrahydroquinoline (2.27 g, 0.015 mol) was converted to present title product as an oil, purified by flash chromatography on 4 cm×40 mm of silica gel with $CH_2Cl_2$ as eluant, 1.84 g.

EXAMPLE 22

5-[(1-Methyl-1,2,3,4-tetrahydro-6-quinolyl)methylene]thiazolidine-2,4-dione

By the method of Example 6, title product of the preceding Example (1.40 g, 0.008 mol) was converted to present title product, 1.50 g; mp 254°-257° C.

EXAMPLE 23

5-[(1-Methyl-1,2,3,4-tetrahydro-6-quinolyl)methyl]thiazolidine-2,4-dione

By the method of Example 15, title product of the preceding Example (1.0 g) was converted to present title product as a solid, 0.67 g, which was recrystallized from ethyl acetate/cyclohexane to recover purified title product in two crops, 0.42 g; mp 122°-125° C.

EXAMPLE 24

5-[1-Methyl-1,2,3,4-tetrahydro-6-quinolyl)methyl]thiazolidine-2,4-dione, Sodium Salt By the method of Example 8, the product of the preceding Example (0.38 g, 0.0014 mol) was converted to present title product, 0.31 g; mp greater than 250° C.

EXAMPLE 25

1-Benzyl-6-formyl-1,2,3,4-tetrahydroquinoline3-spirocyclopentane

By the method of Example 13, 1-Benzyl-1,2,3,4-tetrahydroquinoline-3-spiropentante (0.80 g, 0.0029 mol) was converted to present title product, 0.65 g.

EXAMPLE 26

5-[(Spiro[1-benzyl-1,2,3,4-tetrahydroquinoline-3,1'-cyclopentane]-6-yl)methylene]thiazolidine-2,4-dione By the method of Example 6, title product of the preceding Example (0.63 g, 0.0021 mol) was converted to present title product, 0.33 g; mp 205°–209° C.

EXAMPLE 27

5-[(Spiro[1-benzyl-1,2,3,4-tetrahydroquinoline-3,1'-cyclopentane]-6-yl)methyl]thiazolidine-2,4-dione By the method of Example 7, using radial chromatography on a thick layer silica gel plate with $CHCl_3$ as eluant and without recrystallization, title product of the preceding Example (0.32 g) was converted to present title product 0.23 g; mp 136°–139° C.

EXAMPLE 28

5-[(Spiro[1-benzyl-1,2,3,4-tetrahydroquinoline-3,1'-cyclopentane]-6-yl)methyl]thiazolidine-2,4-dione, Sodium Salt By the method of Example 4, title product of the preceding Example (0.18 g, 0.00044 mol) was converted to present title product, 0.058 g; mp 106°–109° C. (dec.).

EXAMPLE 29

2-Benzyl-1-(2-phenylethyl)-1,2,3,4-tetrahydroquinoline-6-carbaldehyde

By the method of Example 5, 2-benzyl-1-(2-phenylethyl)quinoline (1.05 g, 0.0032 mol) was converted to crude title product, 1.30 g, as an oil. The latter was radially chromatographed on a thick layer plate of silica gel, eluting with $CHCl_3$. The third running fraction gave purified title product, 1.14 g, still as an oil; tlc Rf 0.25 ($CHCl_3$).

EXAMPLE 30

5-[(2-Benzyl-1-(2-phenylethyl)-1,2,3,4-tetrahydro-6-quinolyl)methylene]thiazolidine-2,4-dione By the method of Example 14, without recrystallization, title product of the preceding Example (0.98 g, 0.0028 mol) was converted to present title product, 1.36 g.

EXAMPLE 31

5-[(2-Benzyl-1-(2-phenylethyl)-1,2,3,4-tetrahydro-6-quinolyl)methyl]thiazolidine-2,4-dione By the method of Example 7, using $CHCl_3$ as the eluant on chromatography, title product of the preceding Example (1.2 g, 0.0026 mol) was converted to present title product, the second component to elute, 0.47 g as a foam.

EXAMPLE 32

5-[(2-Benzyl-1-(2-phenylethyl)-1,2,3,4-tetrahydro-6-quinolyl)methyl]thiazolidine-2,4-dione, Sodium Salt By the method of Example 4, title product of the preceding Example (0.30 g, 0.00066 mol) was converted to present title product, 0.22 g; mp 130°–150° C. (decomp.).

EXAMPLE 33

1-Methyl-2-phenyl-1,2,3,4-tetrahydro-6-quinolinecarbaldehyde

By the method of Example 13, 1-methyl-2-phenylquinoline (1.5 g, 0.0067 mol) was converted to present title product, 1.48 g; mp 86°–89° C.

EXAMPLE 34

5-[(1-Methyl-2-phenyl-1,2,3,4-tetrahydro6-quinolyl)methylene]thiazolidine-2,4-dione By the method of Example 14, without recrystallization but with trituration of the product with methanol, the product of the preceding Example (1.38 g, 0.0055 mol) was converted to present title product, 1.49 g; mp 244°–246° C.

EXAMPLE 35

5-[(1-Methyl-2-phenyl-1,2,3,4-tetrahydro-quinolyl)methyl]thiazolidine-2,4-dione

By the method of Example 7, without chromatography, the product of the preceding Example (1.43 g, 0.0041 mol) was converted to present title product, 1.27 g, as a foam.

Anal. Calcd. for $C_{20}H_{20}N_2O_2S$: C, 68.15; H, 5.72; N, 7.95. Found: C, 68.04; H, 5.49; N, 7.66.

EXAMPLE 36

5-[(1-Methyl-2-phenyl-1,2,3,4-tetra-hydro-6-quinolyl)-methyl]thiazolidine-2,4-dione, Sodium Salt By the method of Example 8, the product of the preceding Example (1.20 g, 0.0034 mol) was converted to title product, 0.86 g; mp greater than 280° C.

Anal. Calcd. for $C_{20}H_{19}N_2O_2SNa$: C, 64.15; H, 5.12; N, 7.48. Found: C, 63.42; H, 5.00; H, 7.24.

EXAMPLE 37

2-Benzyl-6-formyl-1,2,3,4-tetrahydronaphthalene-1-spiro-2'-(1',3'-dioxolane)

[Ethylene Glycol Ketal of 2-Benzyl-3,4-dihydro-1(2H)-naphthalenone]

By the method of Example 1, 2-benzyl-6-bromo-1,2,3,4-tetrahydronaphthalene-1-spiro-2'-(1',3'-dioxolane) (1.09 g, 0.003 mol) was converted to present title product, purified by column chromatography on 100 g of silica gel using 1:1 hexane:ether as eluant, 0.29 g; tlc Rf 0.4 (1:1 hexane:ether).

EXAMPLE 38

5-[([2-Benzyl-1,2,3,4-tetrahydronaphthalene-1-spiro-2'(1',3'-dioxolane)]-6-yl)methylene]thiazolidine-2,4-dione By the method of Example 2, the product of the preceding Example (0.29 g, 0.00094 mol) converted to present title product, 0.38 g; tlc Rf 0.6 (9:1 $CH_2Cl_2:CH_3OH$).

EXAMPLE 39

5-[([2-Benzyl-1,2,3,4-tetrahydronaphthalene--spiro-2'-(1',3'-dioxolane)]-6-yl)methyl]thiazolidine-2,4-dione By the method of Example 7, without recrystallization, the product of the preceding Example (0.38 g, 0.00093 mol) was converted to present title product, 0.4 g, as a foam, tlc Rf 0.45 (9:1 CH$_2$Cl$_2$:CH$_3$OH), still containing unreduced starting material (at Rf 0.6).

EXAMPLE 40

5-[(2-Benzyl-3,4-dihydronaphthalen-1(2H)-on-6-yl)methylene]thiazolidine-2,4-dione and 5-[(2-Benzyl-3,4-dihydronaphthalen-1(2H)-on-6-yl)methyl]thiazolidine-2,4-dione The entire product of the preceding Example (0.4 g, contaminated with unreduced olefin) was combined with 15 ml of tetrahydrofuran and 10 ml of 3.5% perchloric acid, stirred for 16 hours, diluted with 50 ml ethyl acetate, and the layers separated. The organic layer was washed 1×50 ml H$_2$O and 1×50 ml saturated brine, dried (MgSO$_4$) and stripped to a foam. The latter was initially chromatographed on 30 g silica gel using 1:1 ether:hexane as eluant. First to be eluted was the olefinic title product, 32 mg as a tan gum; tlc Rf 0.5 (1:1 ether:hexane). The second fraction, 70 mg, contained the second title product, still impure. The latter was rechromatographed on 30 g fresh silica gel, using 2:1 hexane:ether as eluant to yield the second title product in purified form, 58 mg, as a gum; tlc Rf 0.2 (1:1 ether:hexane). The latter was converted to sodium salt by the method of Example 8, 20 mg; mp 288°–289° C. (dec). The mother liquor was stripped, the residue taken up in CH$_2$Cl$_2$, washed in sequence with saturated NaHCO$_3$, H$_2$O and brine, dried (MgSO$_4$) and stripped to recover 18 mg of the second title product.

EXAMPLE 41

5-[(2-Benzyl-1-hydroxy-1,2,3,4-tetrahydro-6-naphthyl)methyl]thiazolidine-2,4-dione The second (reduced) title product of the preceding Example (18 mg, 0.05 mmol) was dissolved in 2 ml each of CH$_2$Cl$_2$ and isopropyl alcohol, and cooled to 0° C. NaBH$_4$ (18 mg, 0.47 mmol) was added and the mixture stirred under N$_2$ for 30 minutes, then held at ambient temperature for 16 hours, recooled, diluted with 20 ml of CH$_2$Cl$_2$, and poured slowly into a like volume of 10% HCl. The aqueous layer was washed with 20 ml of fresh CH$_2$Cl$_2$. The organic layers were combined, washed 1×20 ml H$_2$O and 1×20 ml brine, dried (MgSO$_4$) and stripped to yield title product, 16 mg, as a gum.

EXAMPLE 42

1-[2-(4-Benzyloxyphenyl)ethyl]-1,2,3,4-tetrahydroquinoline-6-carbaldehyde

To dimethylformamide (0.70 ml, 0.009 mol) at 0° C. was added POCl$_3$ (0.82 ml, 0.009 mol), then 1,2-dichloroethane (2 ml) and finally the title product of Preparation O (2.56 g, 0.0075 mol) in 1,2-dichloroethane (2 ml). The resulting mixture was refluxed for 1 hour, cooled and sodium acetate (4.1 g, 0.05 mol) in minimum water added. The resulting mixture further refluxed for 20 minutes, cooled, and the aqueous layer separated and extracted 2×20 ml ether. The organic layers were combined, washed repeatedly with saturated NaHCO$_3$ until gas evolution ceased, dried (MgSO$_4$), and stripped to yield title product, 2.69 g.

By the same method, 1,3-dibenzyl-1,2,3,4-tetrahydroquinoline is converted to 1,3-dibenzyl-1,2,3,4-tetrahydroquinoline-6-carbaldehyde

EXAMPLE 43

5-[[1-(2-(4-Benzyloxyphenyl)ethyl)-1,2,3,4-tetrahydro-6-quinolyl]methylene]thiazolidine-2,4

Additionally triturating the final product with 2×20 ml ether, the title product of the preceding Example (2.5 g, 0.0067 mol) was converted to present title product (1.48 g) according to the method of Example 6.

By the same method, the 1,3-dibenzylquinoline analog of the preceding example is converted to 5-[(1,3-dibenzyl-1,2,3,4-tetrahydro-6-quinolyl)methylene[-thiazolidine-2,4-dione.

EXAMPLE 44

5-[[1-(2-(4-Benzyloxyphenyl)ethyl)-1,2,3,4-tetrahydro-6-quinolyl]methyl]thiazolidine-2,4-dione To the title product of the preceding example (1.20 g) in 25 ml CH$_3$OH was added ground sodium amalgam (15 g). The mixture was stirred for 3 hours, the solids allowed to settle and the methanol decanted. Residual solids were washed 2×10 ml CH$_3$OH. The decant and washes were combined, largely stripped of solvent, diluted with 25 ml H$_2$O, adjusted to pH 3 with dilute HCl, and extracted 3×20 ml CH$_2$Cl$_2$. The organic extracts were combined, dried (MgSO$_4$), and stripped to yield title product, 1.18 g.

By the same method, the 1,3-dibenzylquinoline analog of the preceding Example is converted to 5-[(1,3-dibenzyl-1,2,3,4-tetrahydro-6-quinolyl)methyl]thiazolidine-2,4-dione.

EXAMPLE 45

By the stepwise methods of Examples 1, 2 and 7, various bromine-containing products of Preparation S are converted to:

5-[(6-methyl-5,6,7,8-tetrahydro-2-naphthyl)methyl]-thiazolidine-2,4-dione;

5-[(6-benzyl-6-methyl-5,6,7,8-tetrahydro-2-naphthyl)-methyl]thiazolidine-2,4-dione;

5-[(2-benzyl-5-indanyl)methyl]thiazolidine-2,4-dione;

5-[(2-methyl-5-indanyl)methyl]thiazolidine-2,4-dione;

5-[(2-benzyl-2-methyl-5-indanyl)methyl]thiazolidine-2,4-dione;

5-[(6-benzyl-6,7,8,9-tetrahydro-5H-benzocyclohepten-2-yl)methyl]thiazolidine-2,4-dione;

5-[(6-methyl-6,7,8,9-tetrahydro-5H-benzocyclohepten-2-yl)methyl]thiazolidine-2,4-dione;

5-[(6-benzyl-6-methyl-6,7,8,9-tetrahydro-5H-benzocyclohepten-2-yl)methyl]thiazolidine-2,4-dione;

5-[(5,6,7,8-tetrahydronaphthalene-6-spiro(cyclohexane)-2-yl)methyl]thiazolidine-2,4-dione; and 5-[(7-benzyl-5,6,7,8-tetrahydro-2-naphthyl)methyl]-thiazolidine-2,4-dione.

EXAMPLE 46

By the stepwise methods of Examples 1, 2, 7 and 40, the products of Preparation T are converted to:

5-[(2-methyl-3,4-dihydronaphthalen-1(2H)-on-6-yl)methyl]thiazolidine-2,4-dione;

5-[(2-benzyl-2-methyl-3,4-dihydronaphthalen-1(2H)-on-6-yl)methyl]thiazolidine-2,4-dion 5-[(2-benzyl-indan-1-on-5-yl)methyl]thiazolidine-2,4-dione;

5-[(2-methylindan-1-on-5-yl)methyl]thiazolidine-2,4-dione;

5-[2-benzyl-2-methylindan-1-on-5-yl)methyl]thiazolidine-2,4-dione;

5-[6-benzyl-8,9-dihydro-7H-benzocyclohepten-5(6H)-on-2-yl)methyl]thiazolidine-2,4-dione;
5-[6-methyl-8,9-dihydro-7H-benzocyclohepten-5(6H)-on-2-yl)methyl]thiazolidine-2,4-dione;
5-[(6-benzyl-6-methyl-8,9-dihydro-7H-benzocyclohepten-5(6H)-on-2-yl)methyl]thiazolidine-2,4-dione; and
5-[(7,8-dihydronaphthalen-5(6H)-one-6-spiro(cyclohexane)-2-yl)methyl]thiazolidine-2,4-dione.

EXAMPLE 47

By the method of Example 41, the products of the preceding example are converted to:
5-[(2-methyl-1-hydroxy-1,2,3,4-tetrahydro-6-naphthyl)-methyl]thiazolidine-2,4-dione;
5-[(2-benzyl-2-methyl-1-hydroxy-1,2,3,4-tetrahydro-6-naphthyl)methyl]thiazolidine-2,4-dione;
5-[(2-benzyl-1-hydroxy-5-indanyl)methyl]thiazolidine-2,4-dione;
5-[(2-methyl-1-hydroxy-5-indanyl)methyl]thiazolidine-2,4-dione;
5-[(2-benzyl-2-methyl-1-hydroxy-5-indanyl)methyl]thiazolidine-2,4-dione;
5-[(6-benzyl-5-hydroxy-6,7,8,9-tetrahydro-5H-benzocyclohepten-2-yl)methyl]thiazolidine-2,4-dione;
5-[(6-methyl-5-hydroxy-6,7,8,9-tetrahydro-5H-benzocyclohepten-2-yl)methyl]thiazolidine-2,4-dione;
5-[6-benzyl-6-methyl-5-hydroxy-6,7,8,9-tetrahydro-5H-benzocyclohepten-2-yl)methyl]thiazolidine-2,4-dione.
5-[(5-hydroxy-5,6,7,8-tetrahydronaphthalene-6-spiro(-cyclohexane)-2-yl)methyl]thiazolidine-2,4-dione.

EXAMPLE 48

By conventional methods, the aldehydes of Examples 1, 5, 9, 13, 17, 21, 25, 29, 33 and 37 are reacted with a methyl magnesium halide to form the corresponding 1-substituted ethanol derivatives, and then conventionally oxidized to form, respectively, the following compounds:
2-(6-benzyl-5,6,7,8-tetrahydro-2-naphthyl) acetaldehyde;
2-(1-benzyl-1,2,3,4-tetrahydro-6-quinolyl) acetaldehyde;
2-[1-(2-phenylethyl)-1,2,3,4-tetrahydro-6-quinolyl]acetaldehyde;
2-(1,2-dibenzyl-1,2,3,4-tetrahydro-6-quinolyl]acetaldehyde;
2-(2-benzyl-1-methyl)-1,2,3,4-tetrahydro-6-quinolyl-]acetaldehyde;
2-[1-methyl-1,2,3,4-tetrahydro-6-quinolyl]acetaldehyde;
2-[1-benzyl-1,2,3,4-tetrahydroquinoline-3-spiro(cyclopentane)-6-yl]acetaldehyde;
2-[2-benzyl-1-(2-phenylethyl)-1,2,3,4-tetrahydro-6-quinolyl]acetaldehyde;
2-(1-methyl-2-phenyl-1,2,3,4-tetrahydro-6-quinolyl)acetaldehyde;
2-[2-benzyl-1,2,3,4-tetrahydronaphthalene-1-spiro-2'-(1',3'-dioxolane)-6-yl]acetaldehyde; and
2-[1-(2-(4-benzyloxyphenyl)ethyl)-1,2,3,4-tetrahydro-6-quinolyl]acetaldehyde.

EXAMPLE 49

By the stepwise methods of Examples 2, 7 and, where necessary, 40, the products of the preceding Example are converted to:
5-[1-(6-benzyl-5,6,7,8-tetrahydro-2-naphthyl) ethyl]thiazolidine-2,4-dione;
5-[1-(1-benzyl-1,2,3,4-tetrahydro-6-quinolyl) ethyl]thiazolidine-2,4-dione;
5-[1-(1-(2-phenylethyl)-1,2,3,4-tetrahydro-6-quinolyl)ethyl]thiazolidine-2,4-dione;
5-[1-(1,2-dibenzyl-1,2,3,4-tetrahydro-6-quinolyl) ethyl]thiazolidine-2,4-dione;
5-[1-(2-benzyl-1-methyl-1,2,3,4-tetrahydro-6-quinolyl)ethyl]thiazolidine-2,4-dione;
5-[1-(1-methyl-1,2,3,4-tetrahydro-6-quinolyl) ethyl]thiazolidine-2,4-dione;
5-[1-(spiro[1-benzyl-1,2,3,4-tetrahydroquinoline-3,1'-cyclopentane]-6-yl)ethyl]thiazolidine-2,4-dione.
5-[1-(2-benzyl-1-(2-phenylethyl)-1,2,3,4-tetrahydro-6-quinolyl)ethyl]thiazolidine-2,4-dione;
5-[1-(1-methyl-2-phenyl-1,2,3,4-tetrahydro-6-quinolyl)ethyl]thiazolidine-2,4-dione;
5-[1-(2-benzyl-3,4-dihydronaphthalen-1(2H)-on-6-yl)ethyl]thiazolidine-2,4-dione; and
5-[1-[1](2-(4-benzyloxyphenyl)ethyl)-1,2,3,4-tetrahydro-6-quinolyl]ethyl-thiazolidine-2,4-dione.

EXAMPLE 50

1-[2-(4-Benzyloxyphenyl)ethyl]-2-methyl-1,2,3,4-tetrahydroquinoline-6-carbaldehyde By the method of Example 42, the product of Preparation V (0.78 g, 0.0022 mol) was converted to present title product, purified by radial chromatography on a 4 mm thick layer of silica gel using $CHCl_3$ as eluant. Present title product, 0.48 g, was the second band to elute.

EXAMPLE 51

5-[1-(2-(4-Benzyloxyphenyl)ethyl)-2-methyl-1,2,3,4-tetrahydro-6-quinolyl)methylene]thiazolidine-2,4-dione Except to use a 16 hour reaction time at 140° C., the product of the preceding Example (0.49 g, 0.0013 mol) was converted to present title product, 0.46 g; mp greater than 215° C.

EXAMPLE 52

5-[1-(2-(4-Benzyloxyphenyl)ethyl)-2-methyl-1,2,3,4-tetrahydro-6-quinolyl)methyl]thiazolidine-2,4-dione, Sodium Salt By the method of Example 44, the product of the preceding Example (0.43 g, 0.0089 mol) was converted to the free acid form of present title product as an oil, 0.3 g, purified by radial chromatography on a 2 mm thick plate of silica gel, 0.29 g, oil. The latter (0.18 g) was converted to sodium salt by the method of Example 8, 0.69 g; mp greater than 250° C.

EXAMPLE 53

1-Ethyl-1,2,3,4-tetrahydroquinoline-6-carbaldehyde

By the method of Example 42, the product of Preparation W (2.0 g, 0.012 mol) was converted to present title product as an oil, 1.94 g, purified by column chromatography on silica gel using $CHCl_3$ as eluant, 1.55 g; oil.

EXAMPLE 54

5-[(1-Ethyl-1,2,3,4-tetrahydro-6-quinolyl)methylene]-thiazolidine-2,4-dione

By the method of Example 6, except to use a 2 hour reaction time at 140° C., the product of the preceding Example (1.51 g, 0.0080 mol) was converted to title product, 1.72 g; mp 238–241° C.

EXAMPLE 55

5-[(1-Ethyl-1,2,3,4-tetrahydro-6-quinolyl)methyl]-thiazolidine-2,4-dione, Sodium Salt By the method of Example 44, the product of the preceding Example (1.66 g, 0.0058 mol) was converted to the free acid form of present title product as a foam, 1.10 g, converted to the sodium salt by the method of Example 8, 0.75 g; mp greater than 250° C.

Preparation A

2-Benzyl-6-bromo-3,4-dihydro-1(2H)-naphthalenone

Under dry $N_2$, diisopropylamine (1.7 ml, 0.012 mol) was dissolved in tetrahydrofuran (20 ml) and cooled to −78° C. Butyl lithium (6.88 ml of 1.6 M in hexane, 0.011 mol) was added, and the mixture stirred at −20° C for 0.5 hour and then recooled to −78° C. 6-Bromo-3,4-dihydro-1(2H)-naphthalenone (2.25 g, 0.010 mol; J. Am. Chem. Soc. v. 102, p. 7920, 1980), dissolved in tetrahydrofuran (10 ml) was added, the mixture warmed to −20° C. over 0.5 hour and stirred at that temperature for 15 minutes. Finally benzyl bromide (1.3 ml, 0.011 mol) was added, the mixture warmed over 1 hour to ambient temperature, and stirred at that temperature for 16 hours. The reaction was quenched with two volumes of 10% HCl and extracted with 150 ml ether. The organic layer was washed with 100 ml saturated brine, dried (MgSO$_4$), stripped in vacuo, and the residue chromatographed on silica gel using 1:1 hexane:CH$_2$Cl$_2$ as eluant, monitoring by tlc (1:2 hexane:CH$_2$CL$_2$). Recovered was 380 mg of bis-benzylated product (Rf 0.58), 750 mg of title product (Rf 0.50) and 1.1 g of starting material (Rf 0.28), suitable for recycling.

PREPARATION B

2-Benzyl-6-bromo-1,2,3,4-tetrahydronaphthalene

The title product of the preceding Preparation (0.315 g, 0.001 mol), ethylene glycol (5 ml), NaOH (0.6 g, 0.015 mol) and hydrazine (0.8 ml) were heated together at 180° C. for 4 hours. The reaction mixture was cooled to room temperature, diluted with 100 ml ether, washed in sequence with 25 ml H$_2$O, 25 ml 10° C. HCl and 25 ml saturated NaCl, dried (MgSO$_4$), stripped in vacuo and the residue plug filtered over silica gel to yield title product as an oil, 200 mg; tlc Rf 0.72 (1;1 hexane:CH$_2$Cl$_2$ as eluant).

PREPARATION C

1-Benzyl-1,2,3,4-tetrahydroquinoline 1,2,3,4-tetrahydroquinoline (2.66 g, 0.02 mol), benzaldehyde (3.12 g, 0.03 mol) and glacial acetic acid (0.67 ml, 0.012 mol) were dissolved in methanol (10 ml). Sodium cyanoborohydride (0.675 g, 0.0107 mol) was added portionwise, controlling the resulting vigorous gas evolution by the rate of addition. After 3 hours, the reaction mixture was poured into 50 ml 1N HCl and extracted 3×40 ml ether. The organic layers were combined, dried (MgSO$_4$) and stripped to yield crude title product contaminated with benzyl alcohol. The crude product was dissolved in 50 ml ether, cooled to 0° C. and diffused with HCl gas until precipitation of hydrochloride salt was complete. The ether was decanted from the resulting semi-solid salt. The salt was washed with 20 ml fresh ether, the ether decanted, and the washed salt taken up in 50 ml of fresh ether and 50 ml of H$_2$O. The pH was adjusted to 12 with 1N NaOH, and the ether layer separated, dried (K$_2$CO$_3$) and stripped to 2.47 g of product still containing some residual benzyl alcohol. Repeated conversion to hydrochloride salt and back to free base gave purified title product, 2.02 g.

PREPARATION D 1-(2-Phenylethyl)-1,2,3,4-tetrahydroquinoline

To phenylacetaldehyde (6.0 g, 0.050 mol), 1,2,3,4-tetrahydroquinoline (13 g, 0.1 mol) and acetic acid (0.5 ml) in methanol (50 ml) was added NaBH$_3$CN (1.18 g). After stirring for 1 hour, the mixture was poured into 800 ml 1N HCl and extracted 3×100 ml ether. The combined organic layers were washed 1×100 ml 1N HCl and 2×100 ml H$_2$O, dried (K$_2$CO$_3$) and concentrated to 100 ml. The concentrate was perfused with excess HCl gas to form an oily hydrochloride salt of title product. The solvent was decanted and the residual washed 2×50 ml ether. The washed salt was distributed between excess 5% K$_2$CO$_3$ and ether, and the organic layer separated, dried (K$_2$CO$_3$) and stripped to yield title product as an oil, 6.5 g.

PREPARATION E

2-Benzyl-1,2,3,4-tetrahydroquinoline

Quinoline (6.0 g, 0.0047 mol) in 15 ml of tetrahydrofuran was added to benzyl magnesium bromide (47 ml of 2M in tetrahydrofuran, 0.0094 mol) via a syringe. After stirring for 0.5 hour, the reaction mixture was cooled to 0°, and an equal volume of H$_2$O was added slowly. An exothermic reaction was noted. The aqueous solution was extracted 3×125 ml of ether. The organic layers were combined, dried (K$_2$CO$_3$) and stripped in vacuo to yield intermediate 2-benzyl-1,2-dihydroquinoline as an oil, 11.3 g (0.0051 mol). The latter was taken up in 50 ml of nitrobenzene, refluxed for 2 hours, cooled to room temperature, poured into 150 ml of 1M HCl, and extracted 2×200 ml ether. The aqueous layer was adjusted to pH 8 with saturated NaHCO$_3$ and extracted 3×200 ml ether. The latter ether extracts were combined, dried (MgSO$_4$) and stripped in vacuo to an oil, 4.56 g. The latter was twice chromatographed on a thick layer of silica gel, using 12:1 hexane:ethyl acetate as eluant. In each case, the second band to elute was separated. In this manner 1.3 g of intermediate 2-benzylquinoline was isolated. The latter intermediate (0.5 g, 0.0023 mol) was dissolved in 10 ml of dry ethanol and brought to reflux. Sodium metal (0.8 g) was added over the course of 2 hours. After an additional 1.5 hours of reflux, the contents of the flask began to solidify. The reaction mixture was then cooled to room temperature, stripped of ethanol in vacuo, and the residual solid dissolved in 50 ml of H$_2$O and extracted 3×50 ml benzene. The combined benzene extracts were dried (K$_2$CO$_3$) and stripped to an oil, 0.39 g. The latter was chromatographed on a thick layer plate of silica gel using CHCl$_3$ as eluant to yield purified title product, 0.35 g.

Title product was converted to its hydrochloride salt with dry HCl in ether, and the precipitated salt further purified by sublimation from a bath at 100° C. and 2 mm Hg pressure; m. p. 187–190° C. (softening at 80° C.).

Anal. Calcd. for $C_{16}H_{17}N\cdot HCl$: C, 73.97; H, 6.98; N, 5.39. Found: C, 74.17; H, 7.07; N, 5.25.

PREPARATION F

1,2-Dibenzyl-1,2,3,4-tetrahydroquinoline

Title product of the preceding Preparation (2.0 g, 0.0090 mol) was converted to present title product according to the method of Preparation C, purified in like manner, yielding 0.95 g as an oil. If desired, the product was further purified by silica gel radial chromatography using 15:1 hexane:ethyl acetate as eluant.

PREPARATION G

2-Benzyl-1-methyl-1,2,3,4-tetrahydroquinoline

Title product of Preparation E (2.0 g, 0.0090 mol) was added to a solution of formaldehyde (5.4 ml of 37% aqueous, 0.067 mol) in 27 ml of $CH_3CN$, followed by $NaBH_3CN$ (1.35 g, 0.022 mol).

After 2.5 hours, the pH of the reaction mixture was slowly adjusted to 7 with acetic acid, then stripped in vacuo and the residue taken up in 50 ml 2N KOH. The resulting solution was extracted 3×50 ml ether. The combined organic layers were washed with 50 ml 0.5N KOH, and then with 3×100 ml 1N HCl, dried ($K_2CO_3$) and stripped in vacuo to yield title product as an oil, 1.82 g.

PREPARATION H

1-Methyl-1,2,3,4-tetrahydroquinoline 1,2,3,4-tetrahydroquinoline (2.0 g, 0.0015 mol) and formaldehyde (12 ml of 38% aqueous, 0.015 mol) were combined in 60 ml $CH_3CN$. $NaBH_3CN$ (2.85 g) and then, over a 10 minute period, glacial acetic acid (1.50 ml) were added and the mixture stirred 2 hours, at which time additional acetic acid (0.5 ml) was added. After stirring an additional 30 minutes, the reaction mixture was poured into 200 ml ether, washed 3×30 ml 1N NaOH, dried ($K_2CO_3$) and stripped in vacuo to yield title product, 2.27 g.

PREPARATION I

1-Benzyl-3,4-dihydro-2(1H)-quinolone-3-spirocyclopentane

To diethylamine (0.96 ml, 0.0092 mol) in 4 ml tetrahydrofuran at 0° C. was added butyllithium (5.8 ml of 1.6 M in hexane, 0.0092 mol) and the mixture stirred for 10 minutes at 0° C., then warmed to room temperature, thus forming a solution of lithium diethylimide. The solution was cooled to −22° C., hexamethylphosphoramide (4 ml) and then, over a 5 minutes period, 1-benzyl-3,4-dihydro-2(1H)-quinolone (1.0 g, 0.0042 mol) in 6 ml tetrahydrofuran were added, and the resulting mixture warmed to 15° C. over 1 hour, then recooled to −55° C., at which point a solution of 1-chloro-4-iodobutane (0.95 g, 1.03 molar equivalents) in 10 ml tetrahydrofuran was added over 5 minutes. After stirring 16 hours at −55° C., water (5 ml) was added and the mixture warmed to room temperature, poured into 30 ml $H_2O$ and extracted 3×15 ml ether. The organic layers wre combined, washed 4×20 ml $H_2O$, dried ($MgSO_4$) and stripped to dryness (1.32 g) and radially chromatographed on a thick layer plate of silica gel with $CHCl_3$ as eluant to produce present title product, 0.48 g; mass spectra includes molecular ion at 291.

PREPARATION J

1-Benzyl-1,2,3,4-tetrahydroquinoline-3-spirocyclopentane

To title product of the preceding Preparation (1.06 g, 0.0036 mol) in 25 ml tetrahydrofuran was added $BH_3$:$S(CH_3)_2$ (4.8 ml of 2M in tetrahydrofuran, 0.0096 mol) and the mixture refluxed under $N_2$ for 4 hours, cooled, and concentrated in vacuo. The concentrate was diluted with 10 ml $H_2O$, then 10 ml of 1NHCl, adjusted to pH 10 with $K_2CO_3$, and extracted with 3×20 ml ether. The organic layers were combined, dried ($K_2CO_3$) and stripped in vacuo to yield present title product, 0.90 g.

PREPARATION K

2-Benzyl-1-(2-phenylethyl)quinoline

Title product of Preparation E (2.05 g, 0.0092 mol) was converted to present title product according to the method of Preparation D, partially purified in like manner (conversion to HCl salt and back to base), but with final purification by radial chromatography on silica gel plates using 15:1 hexane:ethyl acetate as eluant, isolating the major band, 1.10 g, as an oil.

PREPARATION L

2-Phenyl-1,2,3,4-tetrahydroquinoline

By the 3-step method of Preparation E, substituting 1M phenyllithium in ether for the benzylmagnesium bromide solution, quinoline (25 g, 0.194 mol) was converted to present title product, 22.4 g, as an oil.

PREPARATION M

1-Methyl-2-phenyl-1,2,3,4-tetrahydroquinoline

By the method of Preparation G, title product of the preceding Preparation (2 g, 0.0096 mol) was converted to present title product, 2.23 g, as an oil. The oil was radially chromatographed on a thick layer plate of silica gel, eluting with 15:1 hexane:ethyl acetate. Purified title product was isolated as the second component to elute, 1.57 g; mp 99°–101° C.

Anal. Calcd. for $C_{16}H_{17}N$: C, 86.05; H, 7.67; N, 6.27. Found: C, 85.79; H, 7.78; N, 6.45.

PREPARATION N

2-Benzyl-6-bromo-1,2,3,4-tetrahydronaphthalene-1-spiro-2'(1',3'-dioxolane) [Ethylene Glycol Ketal of 2-Benzyl-6-bromo-3,4-dihydro-1(2H)-naphthalenone Title product of Preparation A (1.76 g), ethylene glycol (30 ml), p-toluenesulfonic acid (100 mg) and toluene (300 ml) were refluxed for 47 hours, collecting formed water in a Dean-Stark trap. The reaction mixture was cooled, washed with 200 ml $H_2O$ and then 200 ml saturated $NaHCO_3$, dried ($MgSO_4$) and stripped to solids. The latter were triturated with hexane to produce title product, 1.09 g; mp 115°–117° C.; tlc Rf 0.9 (1:1 hexane:ether).

PREPARATION O

2-(4-Benzyloxyphenyl)ethanol

NaH (1.42 g of 60% in oil, 0.036 mol) was washed 2×5 ml hexane and then suspended in tetrahydrofuran (20 ml). 4-Hydroxyphenethyl alcohol (5.0 g, 0.036 mol) was added portionwise and the mixture stirred for 20 minutes to assure complete conversion to the sodium salt. Benzyl bromide (4.2 ml, 1 equivalent) was added and the resulting mixture refluxed for 4 hours, then poured into 50 ml H$_2$O and extracted 3×50 ml ether. The organic layers were combined, extracted 2×20 ml 1N NaOH and then 2×20 ml H$_2$O, dried (MgSO$_4$), stripped, and the solid residue recrystallized from ethyl acetate and cyclohexane to yield title product 4.4 g.

PREPARATION P 2-(4-Benzyloxyphenyl)acetaldehyde

The product of the preceding Preparation (4.20 g, 0.018 mol) was dissolved in CH$_2$Cl$_2$ (50 ml). Diatomaceous earth filter aid (100 cm$^3$) and then pyridinium chlorochromate (6.0 g, 1.5 equivalents) were added and the resulting slurry stirred for 3 hours, then diluted with 200 ml of ether, filtered over a 4 cm×30 mm (height×-width) bed of silica gel, and the filtrate stripped to yield title product, 4.04 g.

PREPARATION Q

1-[2-(4-Benzyloxyphenyl)ethyl]-1,2,3,4-tetrahydroquinoline

The title product of the preceding Preparation (4.0 g, 0.018 mol) was combined with 1,2,3,4-tetrahydroquinoline (4.0 g), stirred for 5 minutes and then diluted with 30 ml CH$_3$OH. NaBH$_3$CN (1.0 g) was added and the mixture stirred for 1 hour, then glacial acetic acid (0.5 ml) added and stirring continued for an additional hour. The mixture was concentrated in vacuo to about 10 ml and the residue diluted with 50 ml each of H$_2$O and ether, the pH adjusted to 2 with diluted HCl and the organic layer separated, washed in sequence 2×50 ml 0.5N HCl, 2×50 ml H2O and 2×50 ml 5% NaHCO$_3$, dried (MgSO$_4$), cooled to 0° C. and the solution saturated with dry HCl to precipitate the hydrochloride salt of title product as an oil. Supernatent ether was decanted and the oil washed with 50 ml of fresh ether, then combined with 50 ml each of H$_2$O and ether and the pH adjusted to 10 with K$_2$CO$_3$. The aqueous layer was separated and extracted with an additional 50 ml ether. The organic layers were combined, dried (K$_2$CO$_3$) and stripped to yield title product as a viscous oil, 2.56 g.

PREPARATION R

By the method of Preparation A, substituting equivalent methyliodide for benzyl bromide, 6-bromo-3,4-dihydro-1(2H)-naphthalenone and 2-benzyl-6-bromo-3,4-dihydro-1(2H)-naphthalenone are converted, respectively, to 2-methyl-6-bromo-3,4-dihydro-1(2H)-naphthalenone and 2-benzyl-2-methyl-6-bromo-3,4-dihydro-1(2H- naphthalenone.

By the same methods, 5-bromo-1-indanone is converted to 2-benzyl-5-bromo-1-indanone, 2-methyl-5-bromo-1-indanone and 2-benzyl-2-methyl-1-indanole; and 2-bromo-8,9-dihydro-5(6H,7H)-benzocycloheptanone is converted to 6-benzyl-2-bromo-8,9-dihydro-5(6H,7H)benzocycloheptanone, 6-methyl-2-bromo-8,9-dihydro 5(6H,7H)-benzocycloheptenone and 6-benzyl-6-methyl-2-bromo-8,9-dihydro-5(6H,7H)-benzocycloheptenone.

By the same method, using 2 equivalents of butyl lithium and a molar equivalent of 1,5-dibromopentane in place of benzyl bromide, 6-bromo-3,4-dihydro-1(2H)-naphthalenone is converted to 6-bromo-3,4-dihydro-1(2H)-naphthalenone-2-spirocyclohexane.

By the same method, 7-bromo-3,4-dihydro-1(2H)naphthalenone is converted to 2-benzyl-7-bromo-3,4- dihydro-1(2H)-naphthalenone; and 1-benzyl-3,4-dihydro-4(1H)-quinolone is converted to 1,3-dibenzyl-3,4-dihydro-4(1H)-quinolone.

PREPARATION S

By the method of Preparation B, the various compounds of the preceding Preparation are converted to:
2-methyl-6-bromo-1,2,3,4-tetrahydronaphthalene;
2-benzyl-2-methyl-6-bromo-1,2,3,4-tetrahydronaphthalene;
2-benzyl-5-bromoindane;
2-methyl-5-bromoindane;
2-benzyl-2-methyl-5-bromoindane;
6-benzyl-2-bromo-6,7,8,9-tetrahydro-5H-benzocycloheptene;
6-methyl-2-bromo-6,7,8,9-tetrahydro-5H-benzocycloheptene;
6-benzyl-6-methyl-2-bromo-6,7,8,9-tetrahydro5H-benzocycloheptene;
6-bromo-1,2,3,4-tetrahydronaphthalene-2-spirocyclohexane;
2-benzyl-7-bromo-1,2,3,4-tetrahydronaphthalene; and
1,3-dibenzyl-1,2,3,4-tetrahydroquinoline.

PREPARATION T

By the method of Preparation N, the products of Preparation O are converted to the ethylene glycol ketals:
2-methyl-6-bromo-1,2,3,4-tetrahydronaphthalene-1-spiro-2'-(1',3'-dioxolane)
2-benzyl-2-methyl-6-bromo-1,2,3,4-tetrahydronaphthalene-1-spiro-2'-(1', 3'-dioxolane);
2-benzyl-5-bromoindane-1-spiro-2'-(1',3'-dioxolane;
2-methyl-5-bromoindane-1-spiro-2'-(1',3'-dioxolane):
2-benzyl-2-methyl-5-bromoindane-1-spiro-2'-(1',3'-dioxolane);
6-benzyl-2-bromo-6,7,8,9-tetrahydro-5H-benzocycloheptene-5-spiro-2'-(1',3'dioxolane);
6-methyl-2-bromo-6,7,8,9-tetrahydro-5H-benzocycloheptene-5-spiro -2'-(1',3'-dioxolane);
6-benzyl-6-methyl-2-bromo-6,7,8,9-tetrahydro-5H-benzocycloheptene-5-spiro-2'-(1',3'-dioxolane);
6-bromo-1,2,3,4-tetrahydronaphthalene-2-spirocyclohexane-1-spiro-2'-(1',3'-dioxolane); and

PREPARATION U

2-Methyl-1,2,3,4-tetrahydroquinoline

2-Methylquinoline (10 g, 0.070 mol) was refluxed in 250 ml ethanol. While refluxing, sodium (22.9 g, 1.0 mol) was added cautiously over a period of 1 hour. The mixture was refluxed for an additional 3.5 hours, cooled to room temperature, poured into 500 ml H$_2$O, and extracted 3×500 ml toluene. The organic layers were combined, dried (K$_2$CO$_3$) and stripped to yield title produce as an oil, 9.2 g.

PREPARATION V

1-[2-(4-Benzyloxyphenyl)ethyl]-2-methyl-1,2,3,4-tetrahydroquinoline

By the method Preparation D, the product of the preceding Preparation (2.41 g, 0.016 mol) and the product of Preparation P (3.70 g, 0.016 mol) were converted to present title product as an oil, 0.78 g.

PREPARATION W

1-Acetyl-1,2,3,4-tetrahydroquinoline 1,2,3,4-Tetrahydroquinoline (5 g, 0.038 mol) and triethylamine (4.55 g, 0.045 mol) were dissolved in 55 ml ether. Acetyl chloride (3.24 g, 0.041 mol) was added and the mixture stirred for 30 minutes, and poured into a mixture of 100 ml 1M HCl and 50 ml ether. The organic layer was separated, washed 1×100 ml 1M HCl and then 2×100 ml 5% NaHCO$_3$, dried (K$_2$CO$_3$) and stripped to yield title product as an oil, 5.13 g.

PREPARATION X

1-Ethyl-1,2,3,4-tetrahydroquinoline

The product of the preceding Preparation (3 g, 0.017 mol) was dissolved in 130 ml of tetrahydrofuran. BH$_3$:S(CH$_2$ (23 ml of 2M in tetrahydrofuran, 0.046 mol) was added and the mixture refluxed for 3 hours, stripped to an oil, and the residue taken up in 1M HCl (77.1 ml; note vigorous reaction). The resulting mixture was heated to obtain a clear solution, adjusted to pH 8 with 1M NaOH, and extracted 3×200 ml ether. The basic extracts were combined; dried (K$_2$CO$_3$) and stripped to yield title product, 2.3 g; oil.

We claim:

1. A compound of the formula

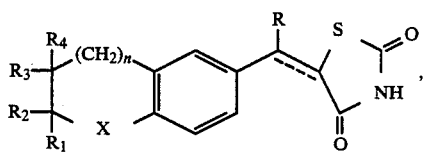

a pharmaceutically acceptable cationic salt thereof, or a pharmaceutically acceptable acid addition salt thereof when the compound contains a basic nitrogen, wherein
the broken line is a bond or no bond;
n is zero, 1, or 2; X is CH$_2$, C=O, CHOH or NR$_5$;
where R$_5$ is hydrogen, (C$_1$-C$_6$)alkyl optionally substituted by OH, Cl, Br, OR$_6$ or COOR$_6$, (CH$_2$)$_x$C$_6$H$_5$ optionally substituted on C$_6$H$_5$ by OH, Cl, Br, OR$_6$ or COOR$_6$, formyl, (C$_2$-C$_5$)alkanoyl, CO(CH$_2$)$_x$C$_6$H$_5$, or COOR$_6$; where x is zero or an integer from 1 to 3 and R$_6$ is benzyl or (C$_1$-C$_4$)alkyl;
R is H, CH$_3$ or C$_2$H$_5$;
when taken separately, R$_1$ is H, (C$_5$-C$_7$)cycloalkyl, (C$_6$-C$_8$)methylsubstituted cycloalkyl, pyridyl, thienyl, furyl, naphthyl, p-biphenylyl, tetrahydrofuranyl, tetrahydrothienyl, tetrahydropyranyl, C$_6$H$_4$W$_2$ or alk-W$_1$ and alk is (C$_1$-C$_6$)alkylene, ethylidene or isopropylidiene; W$_1$ is H, OH, (C$_1$-C$_4$)alkoxy, (C$_1$-C$_4$)thioalkyl, pyridyl, furyl, thienyl, tetrahydrofuryl, tetrahydrothienyl, naphthyl, (C$_5$-C$_7$)cycloalkyl or C$_6$H$_4$W$_2$ and W$_2$ is H, OH, F, Cl, Br, (C$_1$-C$_4$)alkyl, (C$_1$-C$_4$)alkoxy or (C$_1$-C$_4$)thioalkyl; R$_2$ is H or CH$_3$, R$_3$ is H, (C$_1$-C$_6$)alkyl, C$_6$H$_4$W$_2$ or benzyl; and R$_4$ is H;
when R$_1$ and R$_2$ are taken together they form (C$_4$-C$_6$) alkylene and R$_3$ and R$_4$ are each H;
when R$_3$ and R$_4$ are taken together they form (C$_4$-C$_6$) alkylene and R$_1$ and R$_2$ are each H; and
when R$_2$ and R$_3$ are taken together they are (C$_3$-C$_4$ alkylene and R$_1$ and R$_4$ are each H.

2. A compound of claim 1 wherein R is H.
3. A compound of claim 1 wherein the broken line is no bond.
4. A compound of claim 2 wherein the broken line is no bond.
5. A compound of claim 1 wherein n is 1.
6. A compound of claim 2 wherein n is 1.
7. A compound of claim 3 wherein n is 1.
8. A compound of claim 4 wherein n is 1.
9. A compound of claim 8 wherein X is NR$_5$.
10. A compound of claim 9 wherein R$_2$, R$_3$ and R$_4$ are each hydrogen, R$_1$ is hydrogen, phenyl or benzyl, and R$_5$ is methyl, benzyl, or optionally substituted 2-phenylethyl.
11. The compound of claim 10 wherein R$_1$ and R$_5$ are each benzyl.
12. The compound of claim 10 wherein R$_1$ is hydrogen and R$_5$ is 2-(4-benzyloxyphenyl)ethyl.
13. The compound of claim 9 wherein R$_3$ and R$_4$ are each hydrogen, R$_1$ and R$_2$ are taken together as (CH$_2$)$_4$ and R$_5$ is benzyl.
14. A compound of claim 8 wherein X is CH$_2$.
15. The compound of claim 14 wherein R$_2$, R$_3$ and R$_4$ are each hydrogen and R$_1$ is benzyl.
16. A compound of claim 8 wherein X is CHOH.
17. The compound of claim 16 wherein R$_2$, R$_3$ and R$_4$ are each hydrogen and R$_1$ is benzyl.
18. A compound of claim 8 wherein X is C=O.
19. The compound of claim 18 wherein R$_2$, R$_3$ and R$_4$ are each hydrogen and R$_1$ is benzyl.
20. A pharmaceutical composition for use in a hyperglycemic mammal which comprises a blood glucose lowering amount of a compound of claim 1 and a pharmaceutically acceptable carrier.
21. A pharmaceutical composition for use in a hyperglycemic mammal which comprises a blood glucose lowering amount of a compound of claim 9 and a pharmaceutically acceptable carrier.
22. A method of lowering the blood glucose in a hyperglycemic mammal which comprises administering to a mammal in need of such treatment a blood glucose lowering effective amount of a compound of claim 1.
23. A method of lowering blood glucose in a hyperglycemic mammal which comprises administering to a mammal in need of such treatment a blood glucose lowering effective amount of a compound of claim 9.

* * * * *